United States Patent
Brands et al.

(10) Patent No.: US 7,145,002 B2
(45) Date of Patent: Dec. 5, 2006

(54) CRYSTALLINE FORMS OF CARBAPENEM ANTIBIOTICS AND METHODS OF PREPARATION

(75) Inventors: Karel M. J. Brands, Jersey City, NJ (US); Raymond Cvetovich, Scotch Plains, NJ (US); Louis S. Crocker, Belle Mead, NJ (US); Michael D. Ward, Westfield, NJ (US); Amar J. Mahajan, Piscataway, NJ (US); Robert M. Wenslow, East Windsor, NJ (US); John M. Williams, Hillsborough, NJ (US); Daniel R. Sidler, Whitehouse Station, NJ (US); Charles Orella, Whitehouse Station, NJ (US); Elizabeth S. Fisher, Cranbury, NJ (US); Ronald Jobson, East Brunswick, NJ (US)

(73) Assignee: Merck & Co. Inc., Rahway ( * ) Notice: Subject to any disclaimer, the term of this patent is extended or adjusted under 35 U.S.C. 154(b) by 96 days.

(21) Appl. No.: 10/485,319

(22) PCT Filed: Sep. 20, 2002

(86) PCT No.: PCT/US02/30002

§ 371 (c)(1),
(2), (4) Date: Jan. 27, 2004

(87) PCT Pub. No.: WO03/026572

PCT Pub. Date: Apr. 3, 2003

(65) Prior Publication Data

US 2004/0235817 A1      Nov. 25, 2004

Related U.S. Application Data

(60) Provisional application No. 60/325,127, filed on Sep. 26, 2001.

(51) Int. Cl.
C07D 477/20      (2006.01)

(52) U.S. Cl. ..................................................... 540/350
(58) Field of Classification Search ............... None
See application file for complete search history.

(56) References Cited

U.S. PATENT DOCUMENTS

| | | | |
|---|---|---|---|
| 4,888,344 A | 12/1989 | Sunagawa et al. | |
| 4,943,569 A | 7/1990 | Sunagawa | |
| 5,478,820 A | 12/1995 | Betts et al. | |
| 5,641,770 A | 6/1997 | Kwak et al. | |
| 5,648,501 A | 7/1997 | Brands | |
| 5,756,765 A | 5/1998 | Kwak et al. | |
| 5,872,250 A | 2/1999 | Williams et al. | |
| 5,965,747 A | 10/1999 | Brands et al. | |
| 6,063,931 A | 5/2000 | Brands et al. | |
| 6,180,783 B1 | 1/2001 | Williams et al. | |
| 2004/0063931 A1* | 4/2004 | William et al. | 540/350 |
| 2004/0176351 A1* | 9/2004 | Cvetovich et al. | 540/350 |

FOREIGN PATENT DOCUMENTS

EP      0 579 826      8/1993

OTHER PUBLICATIONS

D. E. Bugay et al., "Solid-State Nuclear Magnetic Resonance Spectroscopy: Theory and Pharmaceutical Applications", 1993, pp. 317-327, vol. 10, No. 3, Pharmaceutical Research.
R. K. Harris et al., "Cross-Polarization/Magic-Angle Spinning NMR Studies of Polymorphism: Androstanolone", 1989, 465-469, vol. 45A, No. 4, Spectrochimica Acta.
S. R. Byrn et al., Analysis of Solid-State Carbon-13 NMR Spectra of Polymorphs (Benoxaprofen and Nabilone) and Pseudopolymorphs (Cefazolin), 1985, pp. 565-568, vol. 74, No. 5, J. Pharmaceutical Sciences.
T. K. Natishan et al., "Residual Solvents Determination in the Antibiotic L-749,345 by Static Headspace Gas Chromatography", 1998, pp. 275-281, vol. 800, J. of Chromatography.

* cited by examiner

Primary Examiner—Mark L. Berch
(74) Attorney, Agent, or Firm—Sylvia A. Ayler; Valerie J. Camara

(57) ABSTRACT

A process for preparing a crystalline, carbapenem monosodium salt of formula IIa:

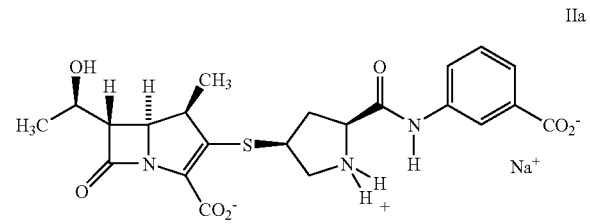

characterized by the steps a) adding about 10 to 30% of an organic solvent to an aqueous solution of the carbapenem, b) cooling the resulting solution to less than −5° C., c) adjusting the pH using a solution containing an acid in an organic solvent to give the appropriate pH for crystallization, and d) crystallizing the compound by adding methanol, and a $C_{2-5}$ alcohol at between −5 and −25° C.

6 Claims, 7 Drawing Sheets

FIG 2

Solvate B

CRYSTALLINE FORMS OF CARBAPENEM ANTIBIOTICS AND METHODS OF PREPARATION

CROSS REFERENCE TO RELATED APPLICATIONS

This application is the National Stage of International Application No. PCT/US02/30002 filed on Sep. 20, 2002 which claims the benefit under 35 U.S.C. 119(e) of U.S. Provisional Application No. 60/325,127 filed on Sep. 26, 2001.

BACKGROUND OF THE INVENTION

Carbapenems are a broad class of antibiotic compounds useful for the treatment of infectious diseases, including gram positive and negative, aerobic and anaerobic bacteria. U.S. Pat. No. 5,478,820 to Betts et al, issued Dec. 26, 1995, now assigned to Zeneca Ltd. (incorporated herein by reference thereto), teaches carbapenem compounds, salts and hydrolysable esters thereof, of the general formula I:

wherein $R^1$ is 1-hydroxyethyl, 1-fluoroethyl or hydroxymethyl, $R^2$ and $R^3$ are hydrogen or $C_{1-4}$ alkyl, and $R^4$ and $R^5$ are hydrogen, halo, cyano, nitro, hydroxy, alkylamino, aminosulphonyl, or carbamoyl.

Crystalline forms of carbapenem antibiotics are desirable for improved purity and stability compared with amorphous forms. Crystallization allows isolation of a compound with rejection of impurities, and crystalline forms tend to be more stable than amorphous forms of the same compound. In the present invention, crystalline forms of the carbapenem (4R,5S,6S,8R,2'S,4'S)-3-[[2-[[(3-carboxyphenyl) amino]carbonyl]pyrrolidin-4-yl]thio]-4-methyl-6-(1-hydroxyethyl)-7-oxo1-azabicyclo [3.2.0]hept-2-en-2-carboxylic acid have been discovered and characterized and the processes for making said forms are disclosed.

The compounds of formula I can generally be synthesized taking into account the disclosure of U.S. Pat. No., 6,063,931 granted May 16, 2000, U.S. Pat. No. 5,648,501 granted Jul. 15, 1997, U.S. Pat. No. 5,478,820 granted Dec. 26, 1995, U.S. Pat. No. 6,180,783 granted Jan. 30, 2001, U.S. Pat. No. 5,872,250 granted Feb. 16, 1999 and U.S. Pat. No. 5,965,747, granted Oct. 12, 1999 (all incorporated herein by reference). See also Bugay, D. E., Pharm. Res., 1993, 10, 317; Harris, R. K., et al., Spectrochimica Acta, 1989, 45A, 465; Byrn, S. R., et al., J. Pharmaceutical Sciences, 1985, 74, 565.

SUMMARY OF INVENTION

Crystalline forms of the carbapenem (4R,5S,6S,8R,2'S,4'S)-3-[[2-[[(3-carboxyphenyl)amino]carbonyl]pyrrolidin-4-yl]thio]-4-methyl-6-(1-hydroxyethyl)-7-oxo1-azabicyclo [3.2.0]hept-2-en-2-carboxylic acid (formula II) and processes for making said forms are disclosed:

Specifically, crystalline forms, which are solvates and hydrates or mixed solvates/hydrates of the monosodium salt IIa, are disclosed. These crystalline forms are useful in the isolation and purification of the carbapenem of formula IIa in the manufacture of an antibiotic product for the treatment of serious infections.

BRIEF DESCRIPTION OF THE DRAWINGS

The invention is described in connection with the following pages, of which:

FIGS. 1, 2, 3, 4, and 5 display the 13C CP/MAS solid-state NMR spectra for the A, B, C, D and E solvates, respectively. FIGS. 1, 2 and 3 display solvates containing methanol. FIGS. 4 and 5 display solvates containing n-propanol (NPA) and isopropanol, respectively.

DETAILED DESCRIPTION OF THE INVENTION

A carbapenem of formula I can be prepared according to several methods known in the art. Generally, these carbapenems can be prepared according to U.S. Pat. No. 4,888,344 to M. Sunagawa, issued Dec. 19, 1989, as well as U.S. Pat. No. 4,943,569 to M. Sunagawa, issued Jul. 24, 1990, as well as U.S. Pat. No. 5,478,820 to Betts et al., issued Dec. 26, 1995, all incorporated herein by reference thereto. Additional starting compounds and methods of preparation are taught in U.S. Pat. No. 5,641,770 to Kwak et al., issued Jun. 24, 1997 and U.S. Pat. No. 5,756,765 to Kwak et al., issued May 26, 1998, incorporated herein by reference hereto.

The compound having the structural formula II:

can be isolated by crystallization as the monosodium salt which is represented by the structural formula IIa:

The crystalline forms of this invention are not thermally stable and do not exhibit distinct, well-defined melting points, but rather undergo decomposition upon heating.

The compound of formula IIa readily converts from one crystalline form to another or from amorphous material to a crystalline form depending upon the composition of the solvent that the compound contacts. In addition to the crystalline forms derived by crystallization, crystalline forms of the compound of formula IIa arising by contact of the compound with mixtures of water and certain alcohols are also disclosed herein. These forms are useful in maintaining crystallinity through washing operations intended to remove impurities and in producing seed that can be used to improve performance of the crystallization.

The crystalline compound of formula IIa loses crystallinity thereby producing amorphous material under dehydrating conditions as when the solid is contacted by dry gas or dry water miscible solvent such as ethanol each of which can result in reducing the water content of the solid to less than about 13%, correcting for residual organic solvent.

The crystalline solids are characterized below by virtue of their X-Ray Powder Diffraction (XRPD) patterns and solid-state nuclear magnetic resonance (NMR) spectra, which are useful in unambiguous identification of the unique forms disclosed herein. The XRPD patterns were collected on a Philips automated powder diffractometer with XRG 3100 control and PW3710 mpd control using CuKα radiation with an accelerating potential of 45 kV and a filament emission of 40 mA. Diffraction patterns were collected from about 2 to about 40 °2Theta. The solid-state NMR spectra were generated using a Bruker DSX 400WB NMR system operating a 100.6 MHz for $^{13}C$ and 400.1 MHz for $^1H$ using a Bruker MAS 400WB BL7 double-resonance probe with a spinning module housing a 7 mm zirconia rotor with either KEL-F® end caps with a liquid seal plug or zirconia endcaps. The solid-state $^{13}C$ NMR spectra were acquired using cross polarization (CP), magic-angle spinning (MAS), and high-power decoupling. Proton and carbon 90° pulse widths were ~4 μsec with a contact time of 2.0 msec. The sample was spun at 7.0 kHz and a total of 600–800 scans were collected with a recycle delay of 7.0 sec. Sample temperature between −20 and −5° C. A line broadening of 10 Hz was applied before FT was performed. Chemical shifts are reported on the TMS scale using the carbonyl carbon of glycine (176.03) as a secondary reference.

Form A:

The crystalline Form A is formed through crystallization from a solution containing a compound of formula IIa or by contact of a solid of formula IIa with a mixture of water, methanol, and 1-propanol. This form is unambiguously characterized as having the XRPD pattern 18.44, 13.09, 8.43, 7.58, 6.48, 6.16, 5.55, 5.14, 4.81, 4.50, 4.26, 4.11, 4.02, 3.85, 3.69, 3.41, 3.35, 3.03, 3.25, 3.12, and 2.87 angstroms. More complete XRPD data pertaining to the compound is shown below in Table 1.

TABLE 1

XRPD pattern for the compound of formula IIa (Form A) crystallized from a mixture of water, methanol, and 1-propanol.

| Angle (°2Theta) | D Spacing (angstroms) | I/Imax (%) |
|---|---|---|
| 4.8 | 18.44 | 100 |
| 6.7 | 13.09 | 41 |
| 10.5 | 8.43 | 38 |
| 11.7 | 7.58 | 41 |
| 13.6 | 6.48 | 72 |
| 14.4 | 6.16 | 62 |
| 16.0 | 5.55 | 39 |
| 17.2 | 5.14 | 44 |
| 18.4 | 4.81 | 63 |
| 19.7 | 4.50 | 60 |
| 20.8 | 4.26 | 64 |
| 21.6 | 4.11 | 59 |
| 22.1 | 4.02 | 66 |
| 23.1 | 3.85 | 63 |
| 24.1 | 3.69 | 93 |
| 26.1 | 3.41 | 83 |
| 26.6 | 3.35 | 67 |
| 27.0 | 3.03 | 71 |
| 27.4 | 3.25 | 71 |
| 28.6 | 3.12 | 63 |
| 31.1 | 2.87 | 83 |

Figure 2:
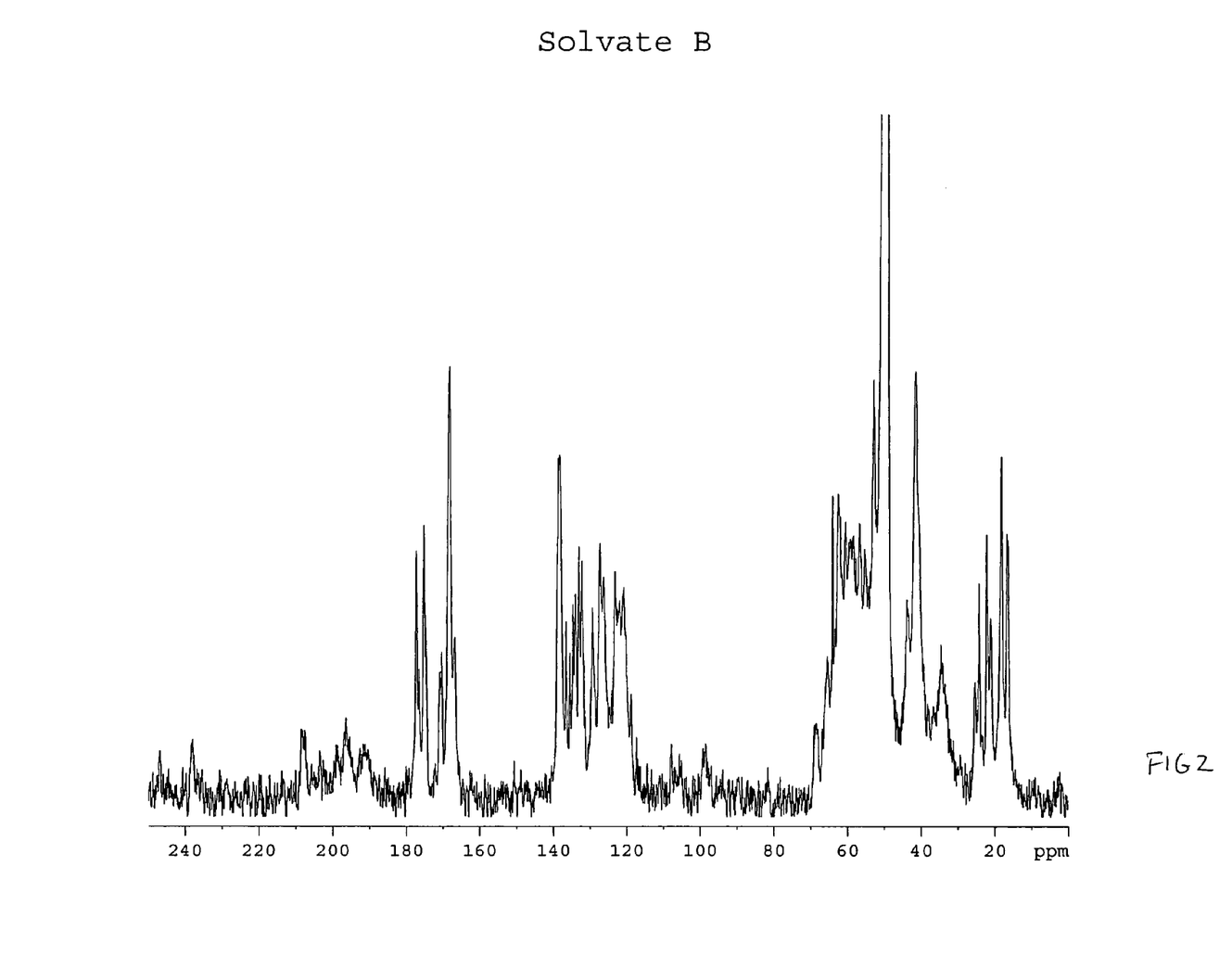

The XRPD pattern corresponding to Table 1 is shown in FIG. 1. The solid-state NMR pattern corresponding to Form A is shown in FIG. 2.

Form B:

The crystalline Form B of the compound of formula IIa is formed through contact of the compound of formula IIa with a mixture of water and 2-propanol and is unambiguously characterized as having the XRPD pattern 18.48, 13.02, 11.27, 8.50, 7.51, 6.51, 6.13, 5.82, 5.13, 4.78, 4.67, 4.50, 4.24, 4.06, 3.85, 3.69, 3.63, 3.41, 3.36, 3.31, 3.22, 3.11, 2.98, 2.87, and 2.77 angstroms. More complete XRPD data pertaining to the compound is shown below in Table 2.

TABLE 2

XRPD pattern for the compound of formula IIa (Form B) contacted with a mixture of water and 2-propanol.

| Angle (°2Theta) | D Spacing (angstroms) | I/Imax (%) |
|---|---|---|
| 4.8 | 18.48 | 59 |
| 6.8 | 13.02 | 24 |
| 7.8 | 11.27 | 21 |
| 10.4 | 8.50 | 49 |

TABLE 2-continued

XRPD pattern for the compound of formula IIa (Form B) contacted with a mixture of water and 2-propanol.

| Angle (°2Theta) | D Spacing (angstroms) | I/Imax (%) |
|---|---|---|
| 11.8 | 7.51 | 34 |
| 13.6 | 6.51 | 55 |
| 14.4 | 6.13 | 51 |
| 15.2 | 5.82 | 27 |
| 17.3 | 5.13 | 32 |
| 18.5 | 4.78 | 58 |
| 19.0 | 4.67 | 64 |
| 19.7 | 4.50 | 62 |
| 20.9 | 4.24 | 58 |
| 21.9 | 4.06 | 100 |
| 23.1 | 3.85 | 39 |
| 24.1 | 3.69 | 46 |
| 24.5 | 3.63 | 65 |
| 26.1 | 3.41 | 51 |
| 26.5 | 3.36 | 37 |
| 26.9 | 3.31 | 34 |
| 27.7 | 3.22 | 75 |
| 28.7 | 3.11 | 32 |
| 30.0 | 2.98 | 33 |
| 31.1 | 2.87 | 47 |
| 32.3 | 2.77 | 49 |

Figure 3:
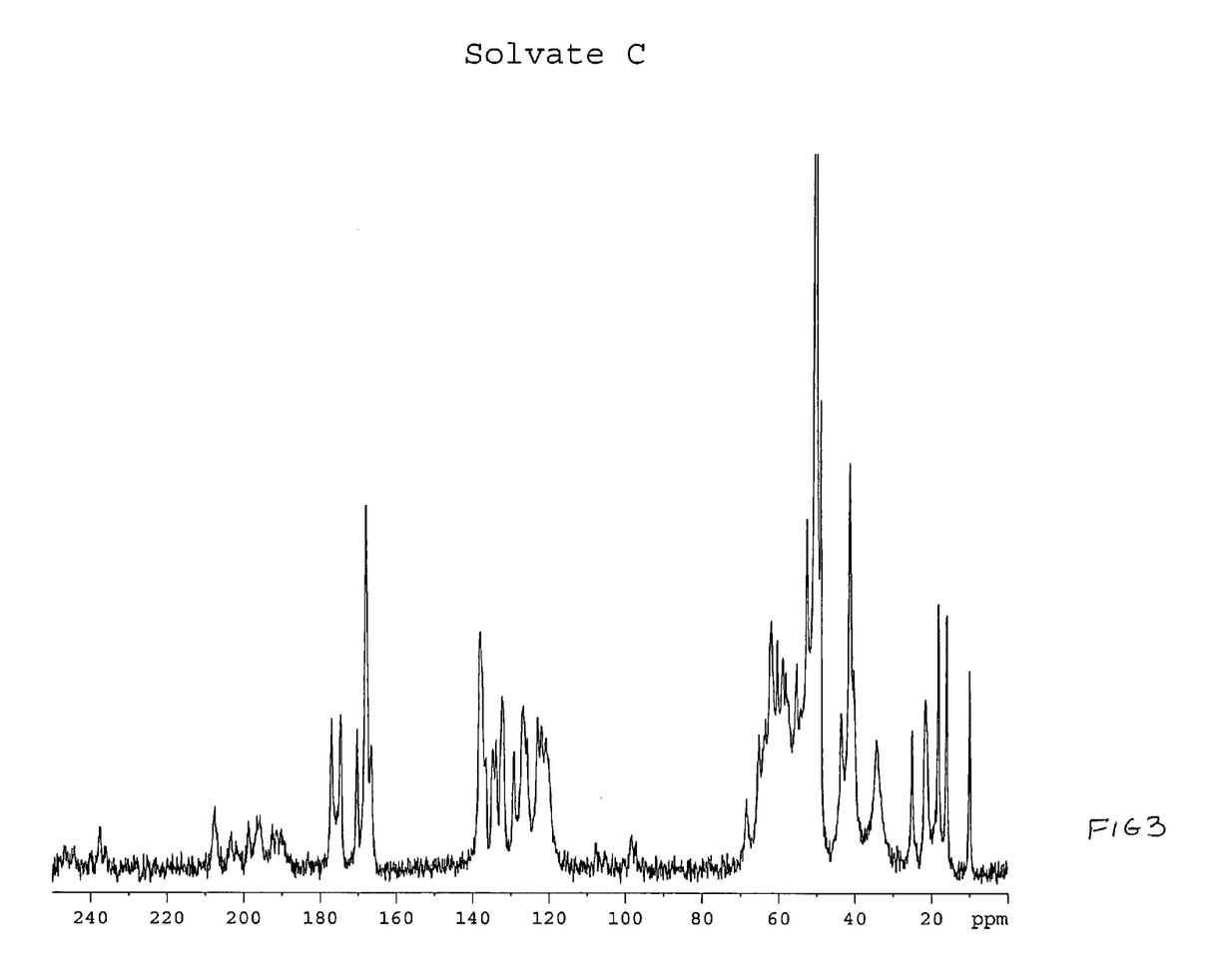
Figure 4:
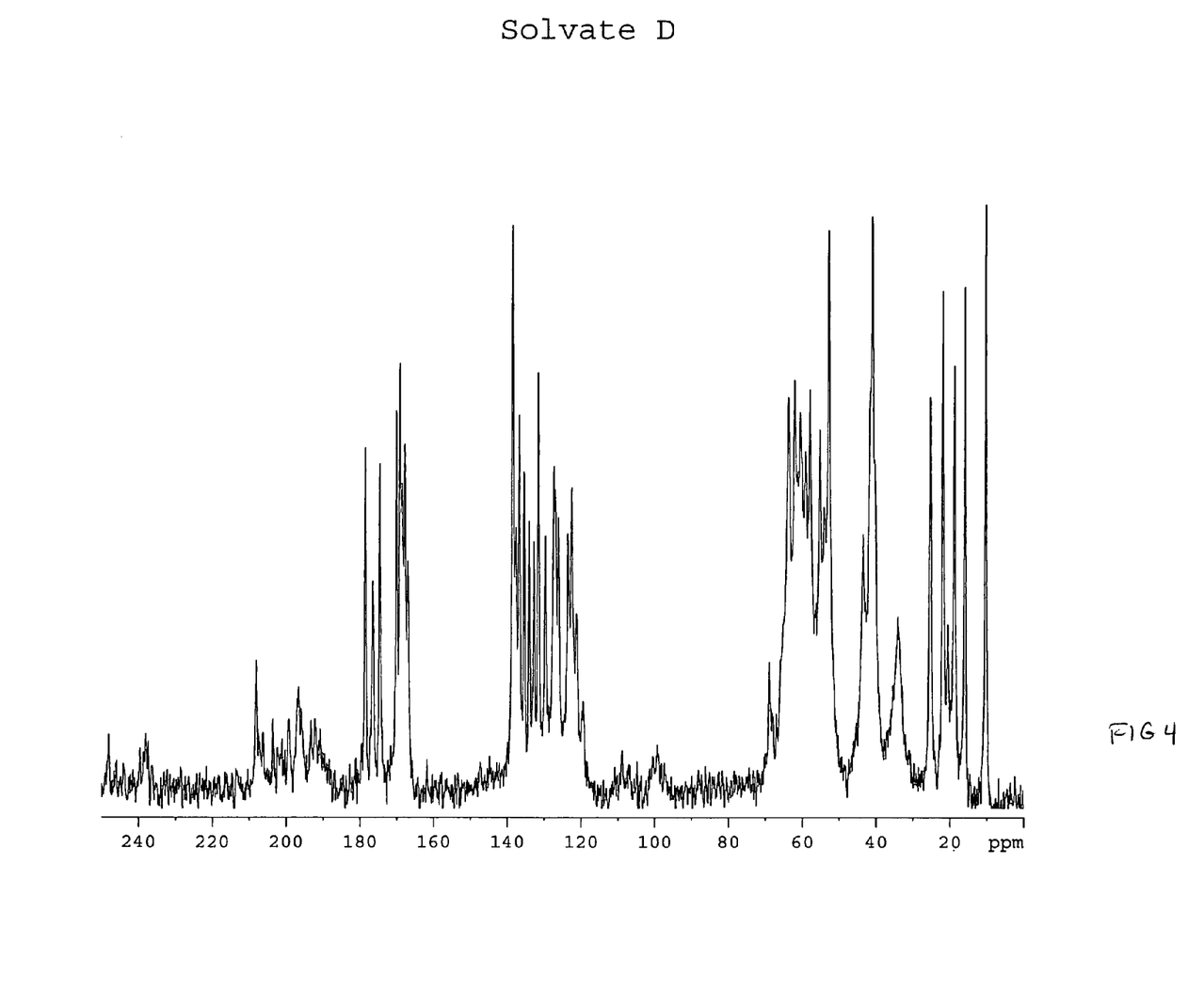
Figure 5:
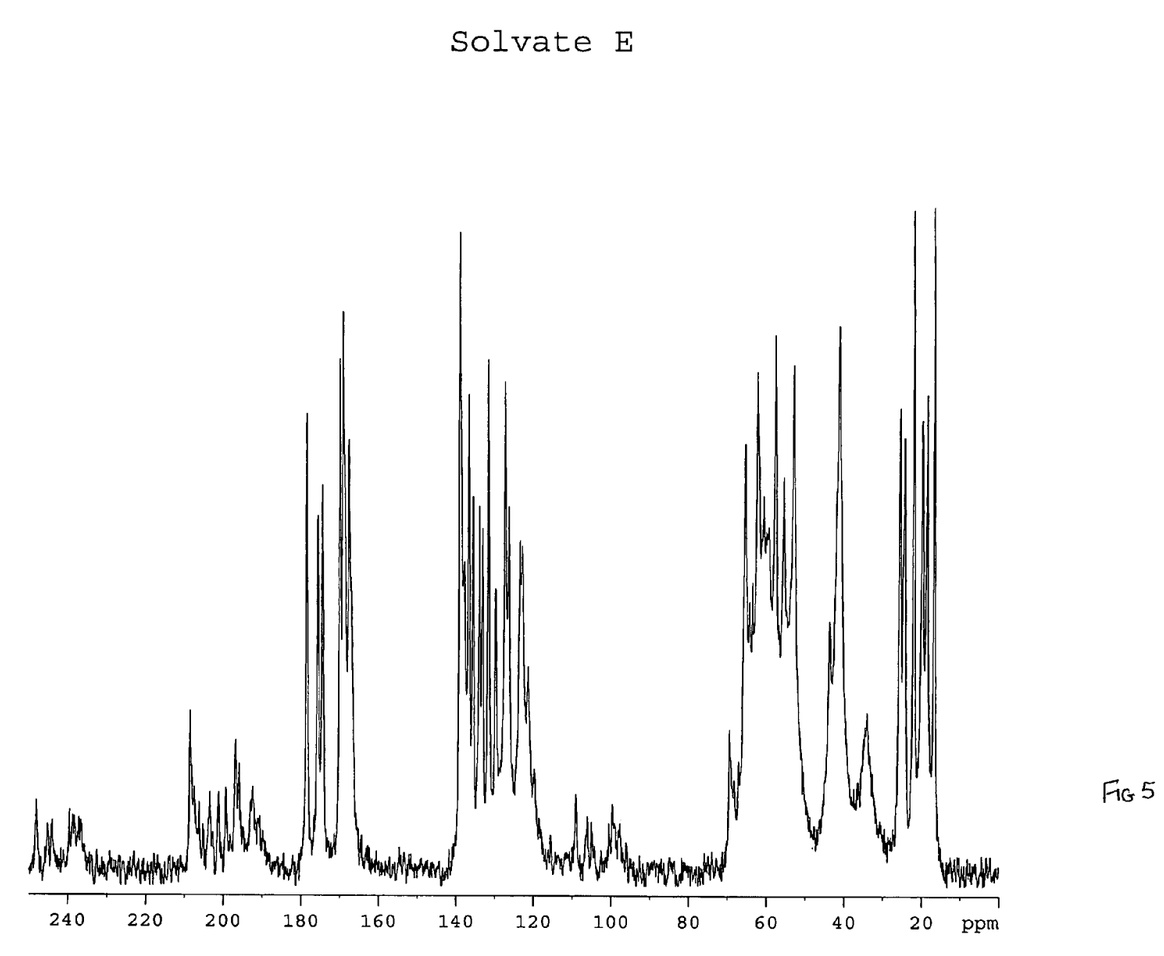
Figure 6:
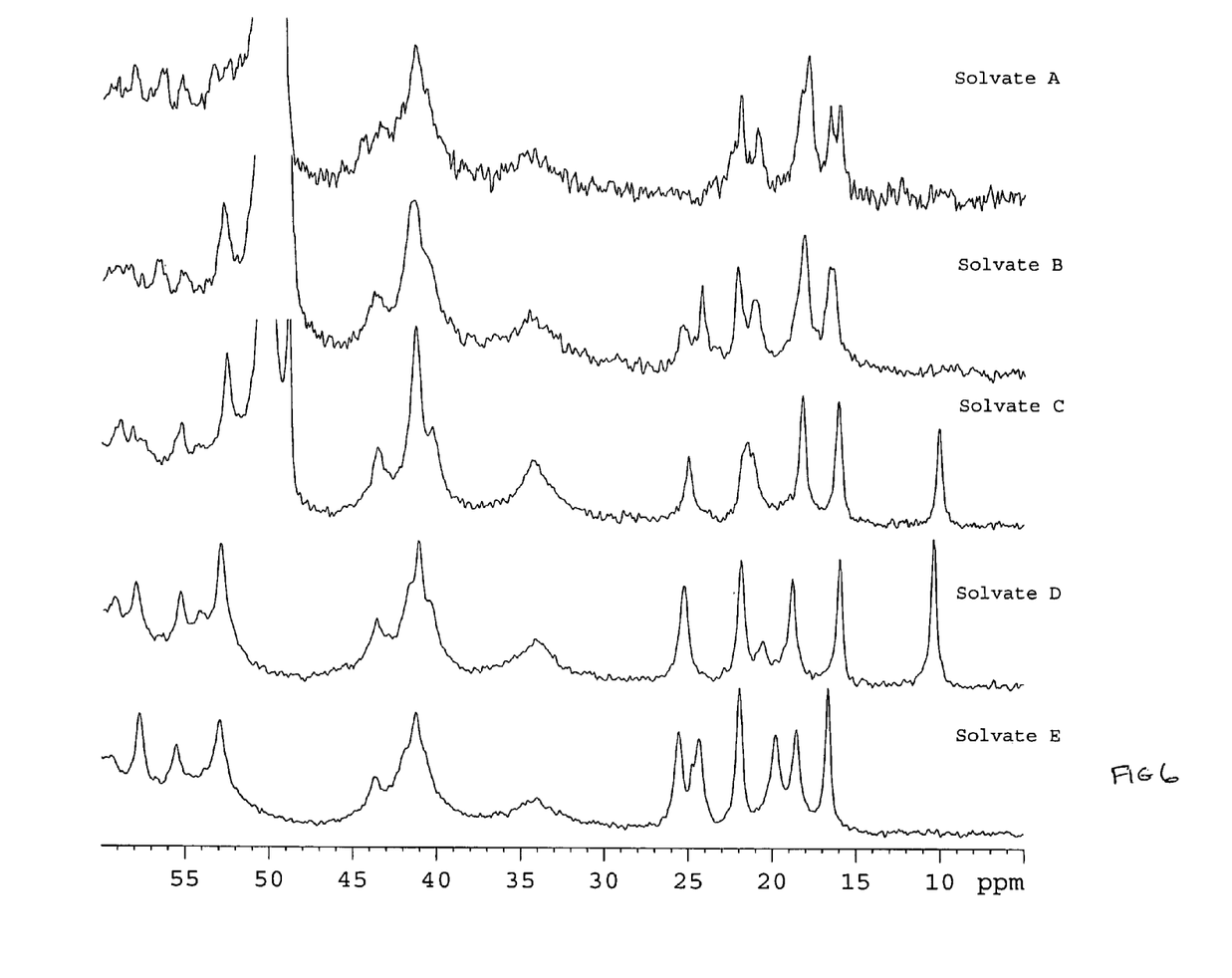
FIGS. 6 and 7 display the unique spectral characteristice of each solvate, A, B, C, D, and E.
Figure 7:
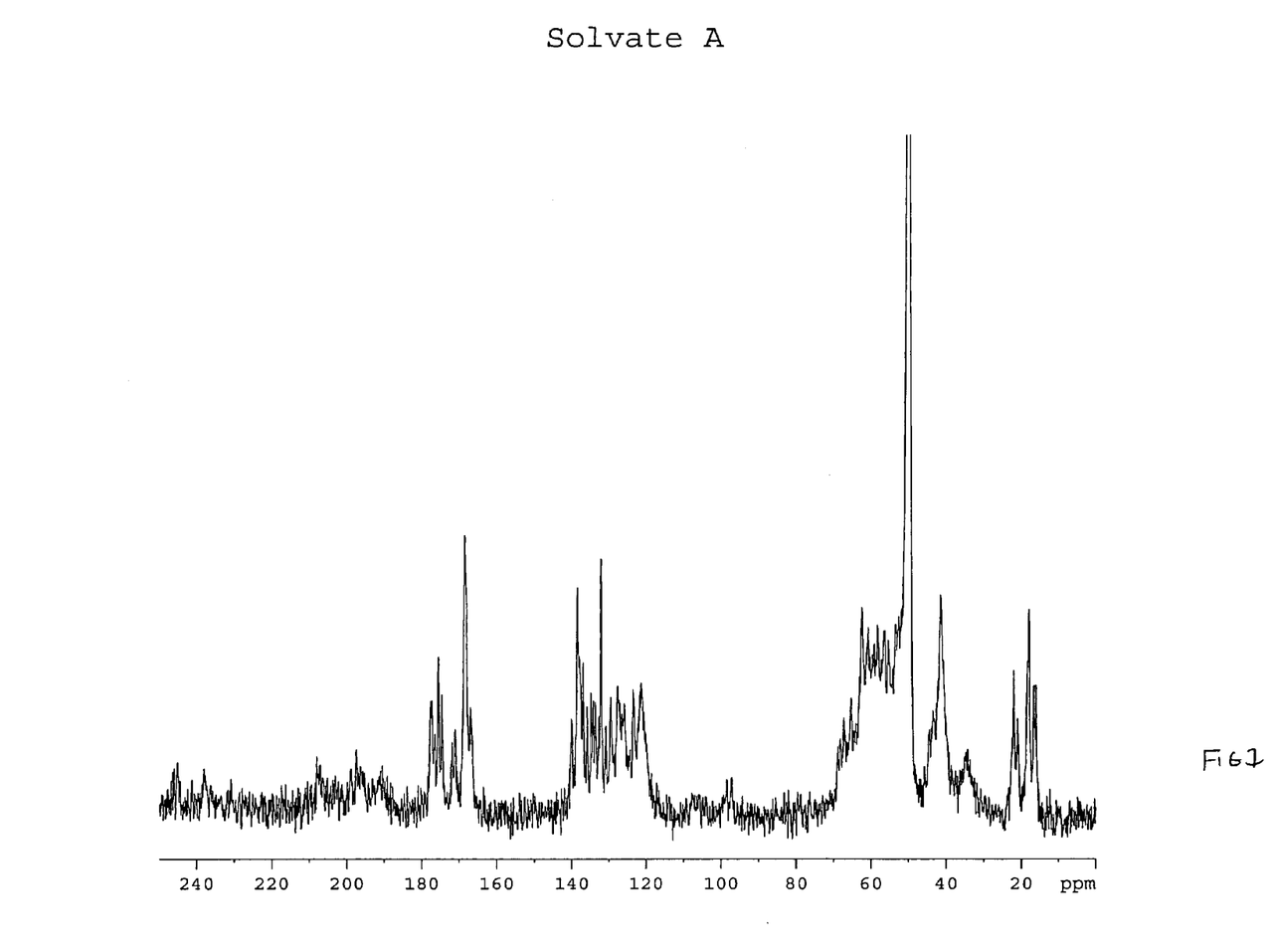

The XRPD pattern corresponding to Table 1 is shown in FIG. 3. The solid-state NMR pattern corresponding to Form B is shown in FIG. 4.

This invention also relates to a process for producing a crystalline carbapenem salt of formula IIa:

comprising adding about 10 to 30% of an organic solvent including but not limited to $C_1$ to $C_5$ alcohols to an aqueous solution containing a compound of formula II, its carbamate form (e.g., structural formula 4) and/or salt forms thereof, cooling the resulting solution to below −5° C., adjusting the pH using a solution of an acid such as formic acid, acetic acid, propionic acid, or hydrochloric acid, preferably acetic acid, in an organic solvent including but not limited to $C_1$ to $C_4$ alcohols, preferably methanol, to give the pH required for crystallization of the compound of formula IIa (pH of about 5 to about 6). The solution is seeded with a slurry containing Compound IIa (up to about 0.5% relative to Compound IIa going into the crystallization) in a mixture of water, methanol, and 1-propanol (10–30, 5–15, and 3–7 mL/g of Compound IIa charged to make the slurry, respectively). The carbamate form of the compound of formula II is formed at the pyrrolidinone nitrogen.

The compound is crystallized by adding from 0.5 to 2 volumes of methanol relative to the aqueous volume, and a $C_{2-5}$ alcohol (from 0.5 to 2.5 volumes relative to the aqueous volume), preferably 1-propanol, at between −5 and −25° C. to give crystalline Form A. The solid is then washed with a mixture of water and 2-propanol (from 5 to 30 mL/g of the compound of formula IIa) with said mixture containing from 5 to 20% water (v/v) to give crystalline Form B.

The crystalline form of formula IIa as crystallized from a solution containing formula IIa in a mixture of water/methanol/1-propanol is also referred to herein as (4R,5S,6S,8R,2'S,4'S)-3-[[2-[[(3-carboxyphenyl)amino]carbonyl]-pyrrolidin-4-yl]thio]4-methyl-6-(1-hydroxyethyl)-7-oxo-1-azabicyclo[3.2.0]hept-2-en-2-carboxylic acid monosodium salt.

The crystalline compound of the present invention is used in the manufacture of a drug product that is useful for the treatment of bacterial infections in animal and human subjects.

The crystalline forms can be produced in accordance with the following non-limiting examples.

EXAMPLE ONE

A hydrogenator is charged with 63 g of 5% Pd on carbon catalyst (dry weight) in 1.8 L of water. The vessel is placed under hydrogen then vented and placed under nitrogen. Sodium hydroxide (68 g, 50%) is charged adjusting the pH to about 7.5 with carbon dioxide.

The enol phosphate (170 g) and the thiol (86 g) are dissolved in 1.3 L of N-ethylpyrrolidinone (NEP). The mixture is cooled to below −40° C. and 1,1,3,3-tetramethylguanidine (109 g) is added. After 3 hours, the reaction mixture is quenched into the hydrogenator at below 15° C. adjusting the pH to about 8 with carbon dioxide. The vessel is placed under hydrogen. When the reaction is complete, the hydrogen is vented and the reaction mixture is treated with activated carbon and filtered. The filtrate is extracted with iso-amyl alcohol containing diphenylphosphoric acid (240 g) and 50% NaOH (44 g). The resulting aqueous solution is further extracted with iso-amyl alcohol to give an aqueous solution containing at least 90 mg/mL of the compound of formula II (predominantly in the stabilized form, 4). Both extractions are performed using two CINC (Costner Industries Nevada Corporation) centrifugal separators set in series for countercurrent extraction. 1-Propanol is added (20% by volume) and the resulting solution is cooled to below −5° C. The pH is adjusted to 5.5 at below −5° C. using a solution of acetic acid in methanol (3 M). Methanol and 1-propanol are respectively added to 0.5 and 0.25 volumes total relative to the aqueous solution from the extraction. The resulting solution is seeded with a slurry containing 0.1 g of the compound of formula IIa in a mixture of water, methanol, and 1-propanol (2, 1, and 0.5 mL, respectively) prepared at −10° C. The product is then crystallized at below −5° C. by adding methanol and 1-propanol to bring the total of each to one volume relative to the aqueous solution from the extraction and isolated by filtration to give the compound of formula IIa as a crystalline solid (Form A).

EXAMPLE TWO

The solid derived by crystallization from a mixture of water, methanol, and 1-propanol (Form A) is washed with a mixture of water and 2-propanol (15:85 v/v, 10 mL/assay g of compound IIa) at below 10° C. to give the compound of formula IIa as a crystalline solid (Form B).

What is claimed is:

1. Crystalline solvate (4R,5S,6S,8R,2'S,4'S)-3-[[2-[[(3-carboxyphenyl) amino]carbonyl]pyrrolidin-4-yl]thio]-4-methyl-6-(1-hydroxyethyl)-7-oxo 1-azabicyclo[3.2.0]hept-2-en-2-carboxylic acid monosodium salt, formula IIa, having an X-ray powder diffraction pattern of Form B in accordance with FIG. 3.

2. A process for preparing a crystalline solvate carbapenem monosodium salt of formula IIa:

comprising the steps of:
a) adding an organic solvent selected from the group consisting methanol and/or 1-propanol to an aqueous solution containing carbapenems of formula II and 4:

and/or salt forms thereof,
b) cooling the solution to below −5° C.;
c) adjusting the pH to between about 6 and about 5 utilizing an acid;
d) crystallizing by adding to the solution from about 0.5 to about 3.0 volumes of methanol relative to the aqueous solution volume, and optionally, from about 0.5 to about 3.0 volumes of [a C$_{1-5}$ alcohol]1-propanol relative to the aqueous solution volume, thereby producing a slurry of formula IIa carbapenem crystals; and
e) [washing the formula IIa carbapenem crystals with methanol and 1-propanol and] isolating the formula IIa carbapenem crystals of Form A; and
f) washing the formula IIa carbapenem crystals of Form A with water and 2-propanol and isolating the formula IIa carbapenem crystals of Form B.

3. The process according to claim 2, wherein the C$_{1-5}$ alcohol is selected from the group consisting of methanol, 1-propanol, 2-propanol, isopropyl alcohol, ethanol, 1-butanol, 2-butanol, isobutyl alcohol, t-butyl alcohol, 1-pentanol, 2-pentanol, 3-pentanol, isopentyl alcohol and mixtures thereof.

4. A process according to claim 2 which is conducted at a temperature of about −5° C. to about −25° C. and wherein the acid is selected from a group consisting of formic acid, acetic acid, propionic acid, and butyric acid.

5. A process according to claim 4 wherein the acid is acetic acid.

6. A process for preparing a crystalline solvate carbapenem monosodium salt of general formula IIa, Form B:

Form B wherein Form B has an X-ray powder diffraction patter 18.48, 13.02, 11.27, 8.50, 7.51, 6.51, 6.13, 5.82, 5.13, 4.78, 4.67, 4.50, 4.24, 4.06, 3.85, 3.69, 3.63, 3.41, 3.36, 3.31, 3.22, 3.11, 2.98, 2.87, and 2.77 angstroms;
comprising:
  a) adding 1-propanol to an aqueous solution containing carbapenems of formula II and 4:

II

4 and/or salt forms thereof,
  b) cooling the solution to below −5° C.;
  c) adjusting the pH to between about 6 and about 5 utilizing an acid;
  d) crystallizing by adding to the solution from about 0.5 to about 3.0 volumes of methanol relative to the aqueous volume, and from about 0.5 to about 3.0 volumes of 1-propanol relative to the aqueous solution volume; and
  e) isolating the formula IIa Form A carbapenem crystals IIa Form A wherein Form A has an X-ray powder diffraction pattern 18.44, 13.09, 8.43, 7.58, 6.48, 6.16, 5.55, 5.14, 4.81, 4.50, 4.26, 4.11, 4.02, 3.85, 3.69, 3.41, 3,35, 3.03, 3.25, 3.12 and 2.87 angstroms;
  f) washing solids containing formula IIa Form A crystals with a mixture of water and 2-propanol to give the compound of formula IIa, Form B, wherein said mixture contains from about 5% to about 25% water (v/v).

* * * * *